(12) United States Patent
Sloan et al.

(10) Patent No.: US 8,597,312 B2
(45) Date of Patent: Dec. 3, 2013

(54) BLUNT NEEDLES WITH MEANS FOR LOCATING AND OCCLUDING VESSELS

(75) Inventors: Todd Sloan, Medway, MA (US); Jon T. McIntyre, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1372 days.

(21) Appl. No.: 11/446,946

(22) Filed: Jun. 5, 2006

(65) Prior Publication Data

US 2007/0282357 A1    Dec. 6, 2007

(51) Int. Cl.
*A61B 17/08*    (2006.01)

(52) U.S. Cl.
USPC ............ 606/158; 606/139; 606/142; 606/157

(58) Field of Classification Search
USPC ................................... 606/157–158
See application file for complete search history.

(56) References Cited

U.S. PATENT DOCUMENTS

| | | | |
|---|---|---|---|
| 6,546,933 B1 | 4/2003 | Yoon | |
| 6,626,916 B1 * | 9/2003 | Yeung et al. | 606/139 |
| 7,169,157 B2 * | 1/2007 | Kayan | 606/148 |
| 2001/0014805 A1 | 8/2001 | Burbank et al. | |
| 2002/0087169 A1 * | 7/2002 | Brock et al. | 606/139 |
| 2003/0120306 A1 | 6/2003 | Burbank et al. | |
| 2003/0233142 A1 * | 12/2003 | Morales et al. | 623/2.37 |
| 2004/0147943 A1 * | 7/2004 | Kobayashi | 606/158 |
| 2004/0153107 A1 * | 8/2004 | Kayan et al. | 606/158 |
| 2008/0208217 A1 * | 8/2008 | Adams | 606/143 |
| 2008/0208226 A1 * | 8/2008 | Seibold et al. | 606/158 |

* cited by examiner

*Primary Examiner* — Corrine M McDermott
*Assistant Examiner* — Son Dang
(74) *Attorney, Agent, or Firm* — Fay Kaplun & Marcin, LLP

(57) ABSTRACT

A device for occluding a blood vessel, comprises a blunt dissection needle and a first occlusion clip releasably mounted to a distal end of the blunt dissection needle, the first occlusion clip being biased to assume a clamped configuration in combination with a retaining element which, in a first configuration, retains the first occlusion clip in an insertion position against an outer surface of the blunt dissection needle and, in a second configuration, releases the first occlusion clip to assume the clamped configuration.

7 Claims, 2 Drawing Sheets

BLUNT NEEDLES WITH MEANS FOR LOCATING AND OCCLUDING VESSELS

BACKGROUND

Conventional treatments to alleviate the symptoms of uterine fibroids include drug therapies which are generally effective only in less advanced cases, myomectomies to remove individual larger fibroids and, for more advanced cases, hysterectomies. Less invasive alternative procedures are often preferable as they typically reduce side effects and involve fewer side effects and shorter hospital stays.

These less invasive procedures include the shrinkage of fibroids using probes that delivery electrical energy, heat or cryogenic cooling to the tissue and procedures involving occlusion of the blood supply to the fibroids. Some of these vascular occlusion procedures including, for example, embolization and mechanical constriction of blood vessels, are complex and may require multiple incisions to reach the target tissue and/or to place devices accurately in desired positions relative to target anatomical structures.

SUMMARY OF THE INVENTION

In one aspect, the present invention is directed to a device for occluding a blood vessel, comprises a blunt dissection needle and a first occlusion clip releasably mounted to a distal end of the blunt dissection needle, the first occlusion clip being biased to assume a clamped configuration in combination with a retaining element which, in a first configuration, retains the first occlusion clip in an insertion position against an outer surface of the blunt dissection needle and, in a second configuration, releases the first occlusion clip to assume the clamped configuration.

The present invention is also directed to a method of treating uterine fibroids, comprising forming an incision in a side of a vaginal fornix proximate to a uterine artery and advancing a distal end of a blunt dissection needle through the incision to a position adjacent to the uterine artery in combination with deploying an occlusion clip from the blunt dissection needle to clamp the uterine artery, the occlusion clip being biased toward a clamping configuration and withdrawing the blunt dissection needle leaving the occlusion clip on the uterine artery. The uterine artery may then be released after a predetermined time has elapsed to restore blood flow therethrough.

DETAILED DESCRIPTION

Figure 1:
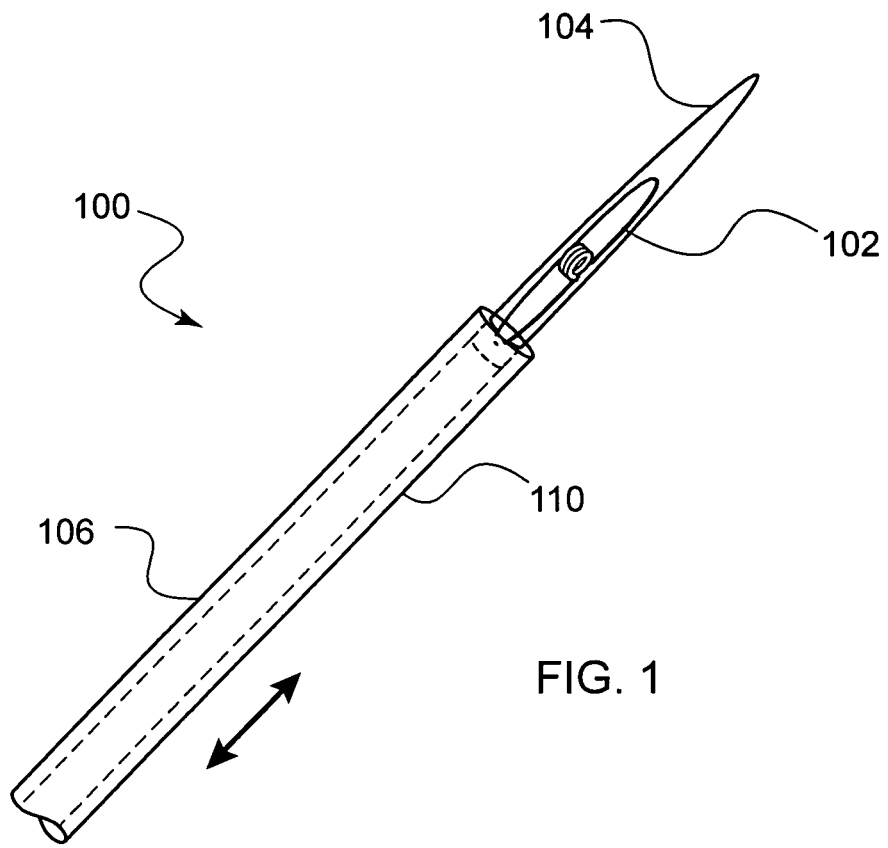
FIG. 1 is a side elevation view showing a blunt needle device to occlude a blood vessel according to an embodiment of the invention.

The present invention may be further understood with reference to the following description and to the appended drawings, wherein like elements are referred to with the same reference numerals. The present invention relates to methods and devices for reducing or stopping the flow of blood to fibroids or other target tissue within an organ (i.e. the uterus). In particular, the present invention relates to minimally invasive methods and devices for occluding blood flow through the uterine arteries.

Embodiments of the present invention provide a system and method for occlusion of selected blood vessels reducing the need for specialized equipment such as, for example, radiological equipment as well as for the services of a specialist such as a radiologist. Procedures according to the present invention for treating tissue masses such as uterine fibroids take advantage of the location of the blood vessels supplying the tissue mass(es) to facilitate access thereto. For example, the uterine arteries which provide blood to the uterus and to any fibroids contained therein are located approximately 1 cm from the vaginal fornix. It is therefore possible to access the uterine arteries via the vaginal fornix using, for example, blunt dissection tools, as will be described in greater detail below.

Figure 2:
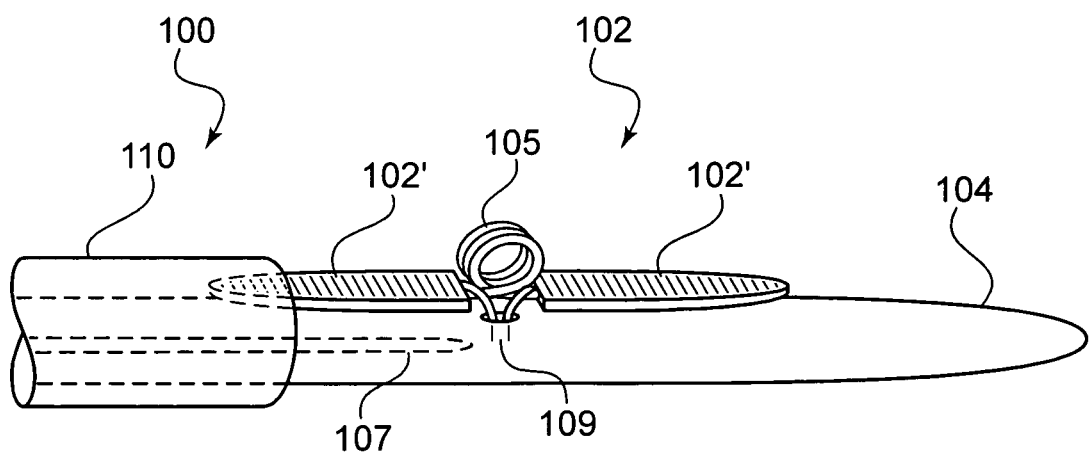
FIG. 2 is a side view of the distal end of the blunt needle device of FIG. 1.
Figure 3:
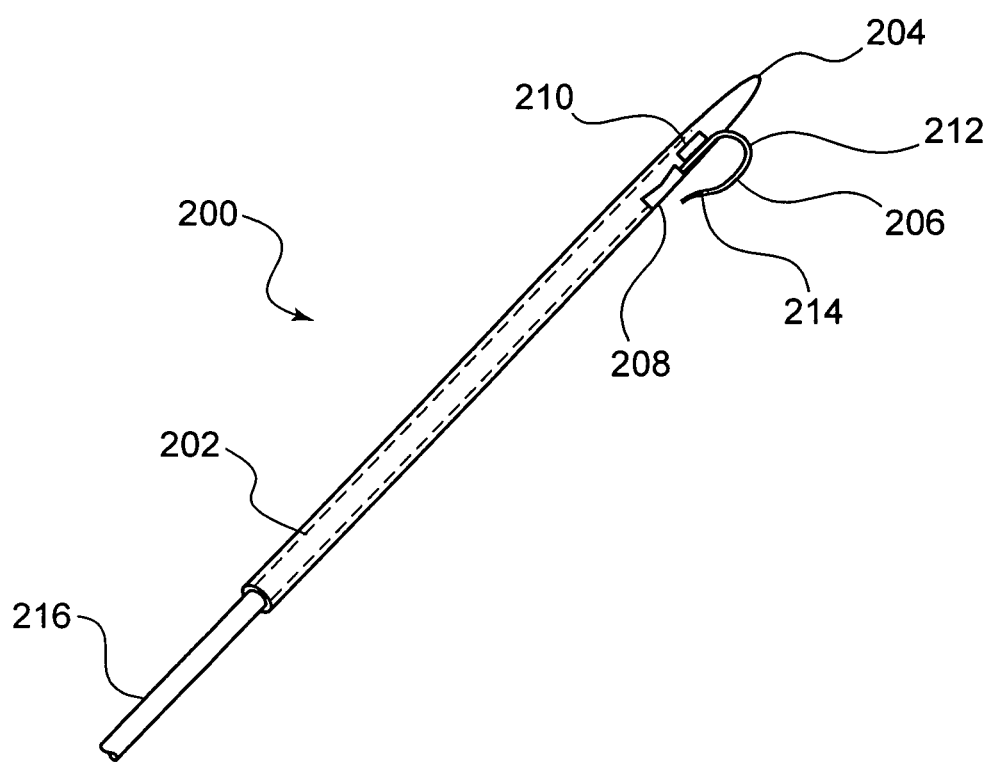
FIG. 3 is a side elevation view showing a second embodiment of a blunt needle device according to the invention, with a suturing mechanism.

FIGS. 1 and 2 show an exemplary embodiment of a device for use in a procedure to locate and occlude vessels supplying blood to a target tissue mass such as a fibroid. In this example, the target tissue mass is a uterine fibroid and the blood vessels are the two uterine arteries. This procedure is minimally invasive, since the uterine arteries are reached through the vaginal fornix, without the need for incisions through the abdomen. According to the invention, a small incision is made in the vaginal fornix at the 3 o'clock position (with reference to the longitudinal axis of the vagina, 12 o'clock being at the top facing the cervix) to access the left uterine artery. The exemplary blunt dissection tool is, in this embodiment, a needle 100 including a distal end 104 formed as would be understood by those skilled in the art to be suitable for penetrating the flesh of the vaginal fornix and passing therethrough until the distal end 104 is adjacent to a first one of the uterine arteries.

The needle 100 includes an occlusion clip 102 including a first jaw member 102' extending along a distal portion of the needle 100 toward the distal end 104 and a second jaw member 102' extending along the distal portion of the needle 100 on a side opposite the first occlusion clip 102. Each of the first and second jaw members 102' is coupled to the needle 100 and to one another via a spring mechanism 105 which biases the clip 102 toward a clipping configuration in which the first and second jaw members 102' project substantially perpendicular to the needle 100 in contact with one another. Although the clip 102 is biased by the spring mechanism 105 toward the clipping configuration, it is held in place thereagainst by a retainer element which, in this embodiment, is formed as an outer tube 110 which is slidable relative to the needle 100 in the directions shown by arrow A in FIG. 1. When in an insertion configuration, a distal portion of the outer tube 110 covers at least a portion of each of the first and second jaw members 102', preventing them from moving radially outward due to the bias of the spring mechanism 105. Once the needle 100 has reached a desired position with the first and second jaw members 102' adjacent to a target uterine artery, the outer tube 110 is moved proximally to expose the clip 102, releasing the clip 102 to move outward to the clipping configuration gripping the target uterine artery and occluding blood flow therethrough. The clip 102 is coupled to the needle by a connecting wire 109.

After the occlusion clip 102 has clamped onto the target uterine artery, it is released from the needle 100 so that the needle 100 may be removed from the body through the incision. For example, once the clips 102 have moved to the clipping configuration gripping the target artery, a cutter 107 may be advanced through the needle 100 to shear the connective wire 109, releasing the clip 102 from the needle 100. The occlusion clip 102 is preferably formed of a biocompatible elastic or resilient material, for example, a metal, a plastic and may be a shape memory alloy or polymer. Those skilled in the art will understand that, where the clip 102 includes a shape memory material, the clip 102 may be formed so that, when released from the constraint of the outer tube 110, the clip 102 automatically moves to the clipping configuration (i.e., reverts to a memorized shape adapted to clamp the target artery). This shape memory reversion to the clipping configuration may be employed in addition to or as an alternative to the spring mechanism 105.

The occlusion clip 102 may be deployed utilizing other methods in addition to the exemplary translating outer tube 110. For example, an optional actuating wire 112 may extend through the dissection needle 100 to connect to the occlusion clip 102 so that, pulling a proximal end of the actuating wire 112 proximally ejects the occlusion clip 102 from the needle 100 onto a blood vessel or other structure positioned adjacent to the distal end 104 of the needle 100. As would be understood by those skilled in the art, other conventional mechanisms may be used to release the occlusion clip 102 or a similar mechanical clamping device from the blunt dissection needle 100, after the distal end 104 has been placed in a desired location adjacent to a blood vessel to be occluded.

After the clip 102 has been deployed, the needle 100 is withdrawn from the first incision and a second needle 100 with another clip 102 thereon is inserted into a second incision proximate to the second (i.e., left) uterine artery (e.g., at the 9 o'clock position of the vaginal fornix). The second needle 100 is advanced into the second incision until the distal end 104 is in a desired position adjacent to the second uterine artery and the second clip 102 is deployed to clamp the second uterine artery in the same manner as the first clip 102 was deployed. Alternatively, a needle 100 may include 2 clips 102 formed on radially opposite sides of the needle 100 so that this single needle 100 may be used to clip both uterine arteries. After the artery or arteries have been successfully occluded, the needle 100 is removed from the body via the vaginal opening. Those skilled in the art will understand the clips may be made of a bioresorbable material designed to maintain the occlusive force on the arteries only for a time during which it is desired to occlude blood flow through the arteries (e.g., a time sufficient to necrose the fibroids but insufficient to permanently damage non-targeted tissue of the uterus). As would be understood by those skilled in the art, this time may be approximately 6 hours or more. Alternatively, the clips may be left in place to permanently occlude flow through the arteries.

As shown in FIG. 2, a blunt dissection tool 200 according to a second embodiment of the present invention includes a suturing mechanism for occluding a blood vessel by tying a suture therearound. The blunt dissection tool 200 comprises a large gauge blunt dissection needle 202 having a distal end 204. The suturing mechanism comprises a needle carrier 206 having a predefined memorized shape. That is, the needle carrier 206 is preferably restrained to remain in a first shape (e.g., straight) while received within the blunt dissection tool 200 and then, when extended therefrom, the needle carrier 206 assumes the desired 'memorized' shape. Those skilled in the art will understand that this may be achieved by simply straightening the needle carrier 206 by inserting it into a confining space within the needle carrier 206 after imparting to it a natural bias toward the desired 'memorized' shape to which it will return as soon as the constraint of the confining space is removed. Alternatively, the needle carrier 206 may be formed of a shape memory material (e.g., Nitinol or any known shape memory polymer) so that, under predetermined conditions (e.g., when mechanically released) the carrier 206 will revert to the 'memorized' shape. As shown in FIG. 2, the needle carrier 206 is shaped to load and drive a needle and suture combination 214 away from the blunt dissection tool 200 and then back toward a needle catch 208.

In one exemplary embodiment, the needle carrier 206 of the suturing mechanism 212 is packaged and stored in the deployed state shown in FIG. 2, to maintain the proper geometry for guiding the needle and suture 214 during the procedure. After removal from the package, the needle with suture 214 is loaded in the needle carrier 206. The carrier 206 is then pushed back to retract into the blunt dissection needle 202 in an insertion state. For example, the insertion configuration may be flush along the dissection needle 202, or elongated within a cavity of said dissection needle 202. The distal tip 204 of the dissection needle 202 is inserted into the incision, and using blunt dissection techniques is advanced to a depth corresponding to the location of one of the two uterine arteries.

The desired location of the distal tip 204 relative to the blood vessels may be determined in different ways. For example, an ultrasound crystal 210 may be disposed near the distal tip 204, to determine the nearest position relative to the uterine artery. The ultrasound crystal may emit acoustic energy that is reflected by the blood vessel, and is received and interpreted to determine the position of the blunt dissection needle 202 relative to the blood vessel. Alternatively, other sensing means to locate the target artery may be used. For example, a microphone may be used in place of the crystal 210, to listen to the sound of flowing blood and to determine based on that sound when the distal tip 204 is in a sufficiently close position to the artery.

Once the blunt dissection needle 202 has been placed in a desired position adjacent to a target uterine artery, the needle carrier 206 is advanced by, for example, moving a plunger 216 distally. The plunger 216 may comprise an actuation device at the proximal handle of the dissection tool 200, where it is accessible to a user of the needle 202. Advancement of the needle carrier 206 directs the needle and suture 214 around the target uterine artery along a predetermined path, until the needle and suture 214 are captured by the needle catch 208. In this mode, the needle carrier 206 acts as a guide for the needle 214, causing it to loop around the artery, with the suture attached thereto.

The needle carrier 206 is returned to the retracted position after guiding the needle and suture 214, for example by withdrawing the plunger 216 proximally and the entire blunt dissection needle 202 is removed through the incision, leaving the loop of suture behind around the uterine artery with ends of the suture loop extending out of the blunt dissection tool 200 so that they are accessible to the user. A knot is then tied with the ends of the suture loop and pushed therealong to ligate the blood vessel. Multiple knots may be made and pushed to the blood vessel, to ensure that the blood vessel remains occluded. This procedure is then repeated to treat the second one of the two uterine arteries to complete the treatment of the uterine fibroids. As with the clips 102 described above, the suture may be formed of bioabsorbable material so that the ligating force applied thereby will relax after the desired time (e.g., the time required to necrose the target tissue while leaving non-targeted tissues unharmed). Alternatively, the suture may be left in place to permanently occlude blood flow.

The present invention has been described with reference to specific exemplary embodiments. Those skilled in the art will understand that changes may be made in details, particularly in matters of shape, size, material and arrangement of parts.

Accordingly, various modifications and changes may be made to the embodiments of the invention. The specifications and drawings are, therefore, to be regarded in an illustrative rather than a restrictive sense.

What is claimed is:

1. A device for occluding a blood vessel, comprising:
   a blunt dissection needle;
   a first occlusion clip releasably mounted to a distal end of the blunt dissection needle, the first occlusion clip being biased to assume a clamped configuration;
   a retaining element which, in a first configuration, encapsulates the first occlusion clip and retains the first occlusion clip in an insertion position against an outer surface of the blunt dissection needle and, in a second configuration, releases the first occlusion clip to assume the clamped configuration; and
   a first anchor member releasably coupling the first occlusion clip to the needle and a separating mechanism actuatable to permanently shear the first anchor member to release the first occlusion clip from the needle.

2. The device according to claim 1, wherein the retaining element comprises an outer tube slidable along the blunt dissection needle.

3. The device according to claim 2, wherein, when the outer tube is in a distal position, a distal end of the outer tube covers the first occlusion clip to retain it against the blunt dissection needle and, when the outer tube is in a proximal position, the first occlusion clip is exposed.

4. The device according to claim 1, further comprising a second occlusion clip releasably mounted to a distal end of the blunt dissection needle, the second occlusion clip being biased to assume a clamped configuration.

5. The device according to claim 4, wherein, in the first configuration, the retaining element retains the second occlusion clip in an insertion position against an outer surface of the blunt dissection needle and, in the second configuration, releases the second occlusion clip to assume the clamped configuration.

6. The device according to claim 4, further comprising a second anchor member releasably coupling the second occlusion clip to the needle and a separating mechanism actuatable to shear the second anchor member to release the second occlusion clip from the needle.

7. The device according to claim 1, wherein the first occlusion clip is formed of a bioresorbable material.

* * * * *